(12) United States Patent
Roervig et al.

(10) Patent No.: US 9,827,373 B2
(45) Date of Patent: Nov. 28, 2017

(54) TORSION SPRING INJECTION DEVICE HAVING AN END-OF-DOSE MECHANISM

(71) Applicant: Novo Nordisk A/S, Bagsvaerd (DK)

(72) Inventors: Simon Roervig, Copenhagen OE (DK); Steffen Hansen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 14 days.

(21) Appl. No.: 14/895,302

(22) PCT Filed: Jun. 2, 2014

(86) PCT No.: PCT/EP2014/061389
§ 371 (c)(1),
(2) Date: Dec. 2, 2015

(87) PCT Pub. No.: WO2014/195270
PCT Pub. Date: Dec. 11, 2014

(65) Prior Publication Data
US 2016/0129187 A1   May 12, 2016

Related U.S. Application Data

(60) Provisional application No. 61/833,566, filed on Jun. 11, 2013.

(30) Foreign Application Priority Data

Jun. 4, 2013   (EP) .................................... 13170422

(51) Int. Cl.
*A61M 5/20*   (2006.01)
*A61M 5/315*   (2006.01)
(Continued)

(52) U.S. Cl.
CPC ............ *A61M 5/20* (2013.01); *A61M 5/3155* (2013.01); *A61M 5/3157* (2013.01);
(Continued)

(58) Field of Classification Search
CPC ... A61M 5/3157; A61M 5/20; A61M 5/31568
See application file for complete search history.

(56) References Cited

U.S. PATENT DOCUMENTS

6,454,743 B1   9/2002   Weber
9,155,844 B2 *   10/2015   Brereton ............. A61M 5/2033
(Continued)

FOREIGN PATENT DOCUMENTS

CH   700404 A1   8/2010
EP   338806   10/1989
(Continued)

*Primary Examiner* — Nathan R Price
*Assistant Examiner* — John Doubrava
(74) *Attorney, Agent, or Firm* — Wesley Nicolas (57) ABSTRACT

The present invention relates to a torsion spring based automatic injection device for apportioning set doses of a liquid drug and which injection device is provided with an End-of-Dose feedback mechanism providing a user with an audible signal once the set dose has been injected. During injection, the scale drum rotates back to its "zero" position under influence of the torsion spring. This rotation is halted shortly before reaching the "zero" position by stopping means. The scale drum is thereafter only allowed to continue rotation and thus reach the "zero" position once the torque applied to the scale drum by the torsion spring surpasses a threshold value.

11 Claims, 6 Drawing Sheets

(51) Int. Cl.
*A61M 5/24* (2006.01)
*A61M 5/48* (2006.01)
*A61M 5/32* (2006.01)

(52) U.S. Cl.
CPC ...... *A61M 5/3158* (2013.01); *A61M 5/31553* (2013.01); *A61M 5/31561* (2013.01); *A61M 5/31583* (2013.01); *A61M 5/24* (2013.01); *A61M 5/2466* (2013.01); *A61M 5/486* (2013.01); *A61M 2005/2013* (2013.01); *A61M 2005/2407* (2013.01); *A61M 2005/3267* (2013.01); *A61M 2205/43* (2013.01); *A61M 2205/581* (2013.01)

(56) References Cited

U.S. PATENT DOCUMENTS

| | | | |
|---|---|---|---|
| 2009/0012479 A1* | 1/2009 | Moller | A61M 5/20 604/211 |
| 2012/0245532 A1 | 9/2012 | Frantz et al. | |
| 2012/0277683 A1* | 11/2012 | Moller | A61M 5/31551 604/189 |
| 2012/0283647 A1* | 11/2012 | Cronenberg | A61M 5/31535 604/207 |
| 2015/0202365 A1* | 7/2015 | Roervig | A61M 5/20 604/198 |
| 2016/0008549 A1* | 1/2016 | Plumptre | A61M 5/31541 604/111 |

FOREIGN PATENT DOCUMENTS

| | | |
|---|---|---|
| EP | 594357 A1 | 4/1994 |
| EP | 1909870 A1 | 4/2008 |
| WO | 2006/079481 A1 | 8/2006 |
| WO | 2011003979 A1 | 1/2011 |
| WO | 2011/068531 A1 | 6/2011 |
| WO | 2013/034984 A2 | 3/2013 |
| WO | 2014/001318 A2 | 1/2014 |
| WO | 2014001319 A1 | 1/2014 |
| WO | 2014/161952 A1 | 10/2014 |

* cited by examiner

TORSION SPRING INJECTION DEVICE HAVING AN END-OF-DOSE MECHANISM

CROSS-REFERENCE TO RELATED APPLICATIONS

This application is a 35 U.S.C. §371 National Stage application of International Application PCT/EP2014/061389 (published as WO 2014/195270), filed Jun. 2, 2014, which claims priority to European Patent Application 13170422.3, filed Jun. 4, 2013; this application claims priority under 35 U.S.C. §119 to U.S. Provisional Application 61/833,566; filed Jun. 11, 2013.

THE TECHNICAL FIELD OF THE INVENTION

The present invention relates to a torsion spring injection device for expelling set doses of a liquid drug. The invention especially relates to such torsion spring injection device providing an End-of-Dose feedback signal to the user indicating that the set dose has been ejected. More specifically the invention relates to such torsion spring injection device having the ability to generate the feedback signal with a time delay.

DESCRIPTION OF RELATED ART

Automatic injection devices using a torsion spring to press the liquid drug out from the injection device are widely known.

An almost classic torsion spring injection device which has been known for decades is disclosed in EP 338,806. This specific torsion spring injection device has a dose setting mechanism which can only be operated less than one full revolution which determines an upper limit to the dose size that can be ejected in one operation.

A further development of such torsion spring injection device is disclosed in European patent application No. 133162517 by Novo Nordisk A/S. This torsion spring injection device, which is disclosed in FIG. 1 of the present application, further adds a scale drum which is rotatable for more than one full revolution thereby making it possible to set and eject larger doses of liquid drug. During dose setting the scale drum is rotated in a helical track inside the housing away from its initial position thus successively indicating the size of the set dose through a window in the housing. During dose ejection the scale drum is rotated in the opposite direction back to its initial position such that the number "zero" appears again in the window once the set dose has been ejected.

Also WO 2014/001319 by Novo Nordisk A/S discloses a torsion spring injection device also having a rotatable scale drum. This injection device is disclosed in FIG. 2 of the present application. Here the release of the strained torsion spring and thus the injection is initiated by moving the needle shield in the proximal direction as the injection needle is inserted into the skin.

These injection devices can further be provided with a so-called End-of-Dose feedback mechanism as disclosed in WO 2006/079481. FIGS. 13 to 15 of this WO publication discloses that the spring base is provided with a click arm which is axially strained during the last revolution of the scale drum as the scale drum approaches its initial position during dose ejection. Once the scale drum enters into its initial "zero" position, the strained click arm is released into a countersunk part of the end-surface of the scale drum thus generating an audible signal to the user indicating that the set dose has been ejected.

Other End-of-Dose feedback mechanisms are known from EP 594,357 and U.S. Pat. No. 6,454,743. Common for such mechanism is that the signal is provided immediately when the piston rod has been moved to its new position i.e. at the end of the mechanical part of the injection operation, which not necessary mean that the full set dose of liquid drug has actually been fully delivered. These mechanisms are therefore also often referred to as End-of-Operation mechanism as the signal is provided after the end of the operation of the injection device.

The injection needles normally used has a very little outside diameter and thus a very limited cross-section of the lumen. This restricts the flow through the lumen of the injection needle i.e. when the piston rod has been brought forward the required distance not all the liquid drug has been pressed out, however a pressure has been build up inside the cartridge and the liquid drug will keep flowing through the injection needle for a period of time. As a result, it is recommended to keep the needle inserted in the skin a certain period of time after the injection has been performed in order to make sure that all the liquid drug of the set dose flows into the skin.

Further, most injection devices utilizes a glass cartridge containing the liquid drug and which liquid drug is pressed out through the injection needle by applying a pressure on a rubber plunger moving forward inside the cartridge. This pressure also deforms the rubber plunger why it is recommended to only remove the injection needle from the skin when this rubber plunger has again obtained its non-deformed shape. Often the pressure moving the rubber plunger forward originates from a piston rod abutting the rubber plunger. This abutment also prevents the rubber plunger from settling backwards thus only allowing the rubber plunger to re-settle in the forward direction pressing liquid drug out through the injection needle.

Thus, all together a waiting time of 5 to 10 seconds is recommended before the set dose has been properly ejected from the tip of the injection needle. Since the known injection devices only provides a feedback signal at the end of the mechanical operation of the injection device i.e. once the injection device returns to its "zero" position, the user himself has to time these 5 to 10 seconds either by using a timing device or by counting.

DESCRIPTION OF THE INVENTION

It is an object of the present invention to provide a mechanical based injection device which deliver the End-of-Dose signal with a time delay in relation to the piston rod having been pressed forward (the end of operation) thus indicating to the user that once the audible signal is heard the liquid drug has stopped or almost stopped flowing from the tip of the injection needle.

The invention is defined in claim 1. Accordingly in one aspect the present invention relate to a torsion spring driven injection device for apportioning set doses of a liquid drug and having an End-of-Dose mechanism which provides the EoD signal with some time delay.

The torsion spring based injection device of the invention comprises:
a housing making up the outer shell,
a dose setting mechanism which a user can rotate to set a dose, a rotatable scale drum which is coupled to the dose setting mechanism such that it indicates the size of the set dose as the dose is being set. During dose setting the scale drum rotate away from its "zero" position and during expelling of the set dose it rotates back to its "zero" position. The dose setting away from the "zero" position is conducted by the user operating the dose setting mechanism which also strains the torsion spring whereas the return to "zero" during dosing is driven by the torsion spring.

The "zero" position is the position in which no dose has been set and is indicated by the indicia "0" being visible in the window in the housing usually showing the set dose. However, other indicia than the number "0" can be used to indicate the "no dose set" scenario.

The "zero" position or initial position is defined by a first surface on the scale drum abutting a second surface which in inrotatable in relation to the housing. This second surface can be provided on the housing but could alternatively be provided on an element which is non-rotatable coupled to the housing. This could e.g. be a spring base securing the torsion spring to the housing or it could be a needle shield which telescope in relation to the housing but do not rotate (at least not relatively to the housing). The primary target being that the rotation of the scale drum is stopped when the indicia indicating the "zero" position is aligned with the window or opening in the housing. This stopping in the initial position occurs when the first surface of the scale drum abuts a second surface which is rotational fixed in the housing.

Further, the injection device comprises an End-of-Dose mechanism for generating an audible signal to the user indicating that the rotatable scale drum has returned to its "zero" position.

Usually when this signal is heard, the user has to wait 5-10 seconds before removing the injection needle from the skin in order to make sure that the set dose has actually been delivered into the skin.

However, according to the present invention, the injection device further comprises stopping means which arrests the scale drum before it reaches its "zero" position thereby preventing the feedback signal from being generated. These stopping means is however adapted to allow the scale drum to move pass the stopping means and continue rotation to the "zero" position when the torque applied to the scale drum by the torsion spring surpasses a threshold value.

The idea behind the End-of-Dose mechanism is to counter the torque of the torsion spring with an opposing force when dosing the last unit. What happens is that the torque applied to the scale drum stops because the torque has to work against and overcome the opposing force arising from the pressure build up inside the cartridge. Only when this pressure and thereby the opposing force has dropped below a threshold value will the torque be submitted to the scale drum and rotate it over or pass the stop.

In a preferred form, the stopping means comprises a first member provided on the scale drum and a second member non-rotatable connected to the housing. The rotation of the scale drum is thus halted just before the "zero" position by an engagement between the first element and the second element. When the torque applied to the scale drum by the torsion spring surpasses a certain threshold value (which it does when the pressure inside the cartridge drops below a certain value), the scale drum is allowed to continue its rotation towards its "zero" position. Upon arrival in the "zero" position a click-sound is transmitted. The stopping means is thus both the first element and the second element, and the term "move pass the stopping means" actually refers to the situation in which the engagement between the first element and the second element are released.

Figure 7:
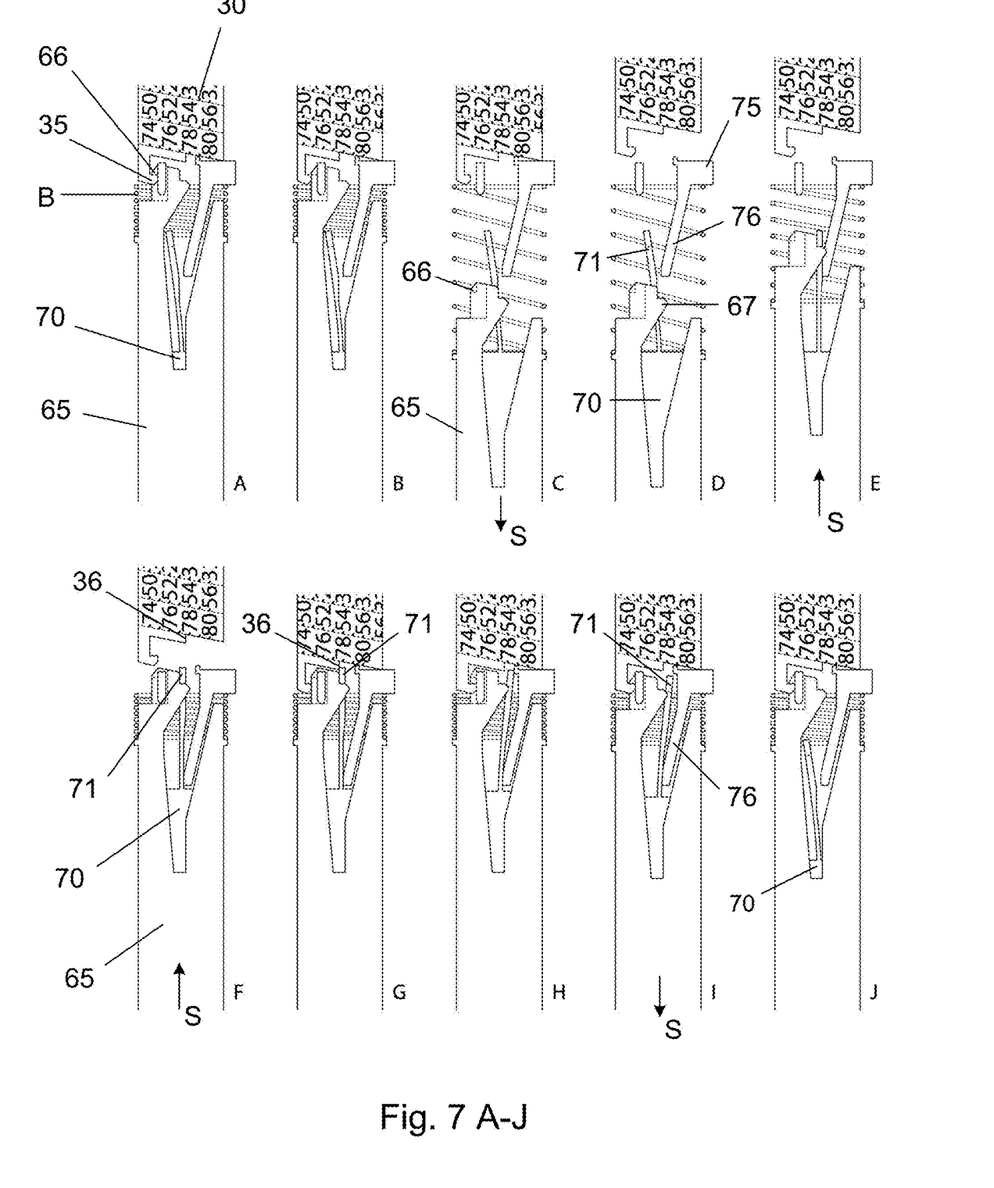

Two different embodiments for the stopping means are given. In one embodiment (FIG. 2+7A-J) the stopping means halting the scale drum is an extension such as an arm or the like extending in a proximal direction from a movable and non-rotatable part of the injection device. The movable part is preferably a needle holder carrying the injection needle as disclosed in WO 2014/001319, which is hereby incorporated by reference.

During dose expelling this extending arm is brought into a position in which it blocks the rotation of the scale drum. The extending arm which is flexible at least in the rotational direction of the scale drum is temporally locked such that it at least temporally prevents the scale drum form returning to its "zero" position.

The extending arm is preferably locked by a click mechanism such as a hook or the like provided on a telescopically movable needle shield. The holding force of this click mechanism determines the threshold value that the torque of the torsion spring need to apply to the scale drum in order to release the click mechanism and return the scale drum to its "zero" position.

In the other embodiment (FIG. 1+3-6), the housing, or rather a spring base permanently connected to the housing, is provided with a flexible arm which can be strained by the return of the scale drum as disclosed in EP application No.: 13162517, which is hereby incorporated by reference.

A stop preferably formed as a protrusion is provided on the proximal end surface of the scale drum. The result being that this stop is arrested by the flexible arm during the return of the scale drum.

Only when the torque applied to the scale drum by the torsion spring passes a threshold value can this flexible arm overcome the holding force of the stop and return the scale drum to its "zero" position.

As explained, the torque of the torsion spring has to overcome both the opposing force arising from the pressure in the cartridge and the counter force arising from the stopping means. Only when the opposing force falls below a certain value will the torque submitted to the scale drum become able to overcome the counter force of the stopping means and thus be able to return the scale drum to its "zero" position.

The flexible arm is preferably provided with a distally pointing protrusion at its free end. This protrusion can further be provided with an angled surface cooperating with a similar angled surface on the stop protrusion. Once the distally provided protrusion of the flexible arm has passed the stop it drops into a countersunk area on the proximal end surface of the scale drum thus providing an audible signal that the scale drum has returned to its "zero" position with a time delay. Once the user hears this time delayed End-of-Dose signal he can immediately remove the injection needle from his skin assured that the liquid drug has been correctly delivered into the skin.

EXAMPLE OF THE INVENTION

Figure 8:
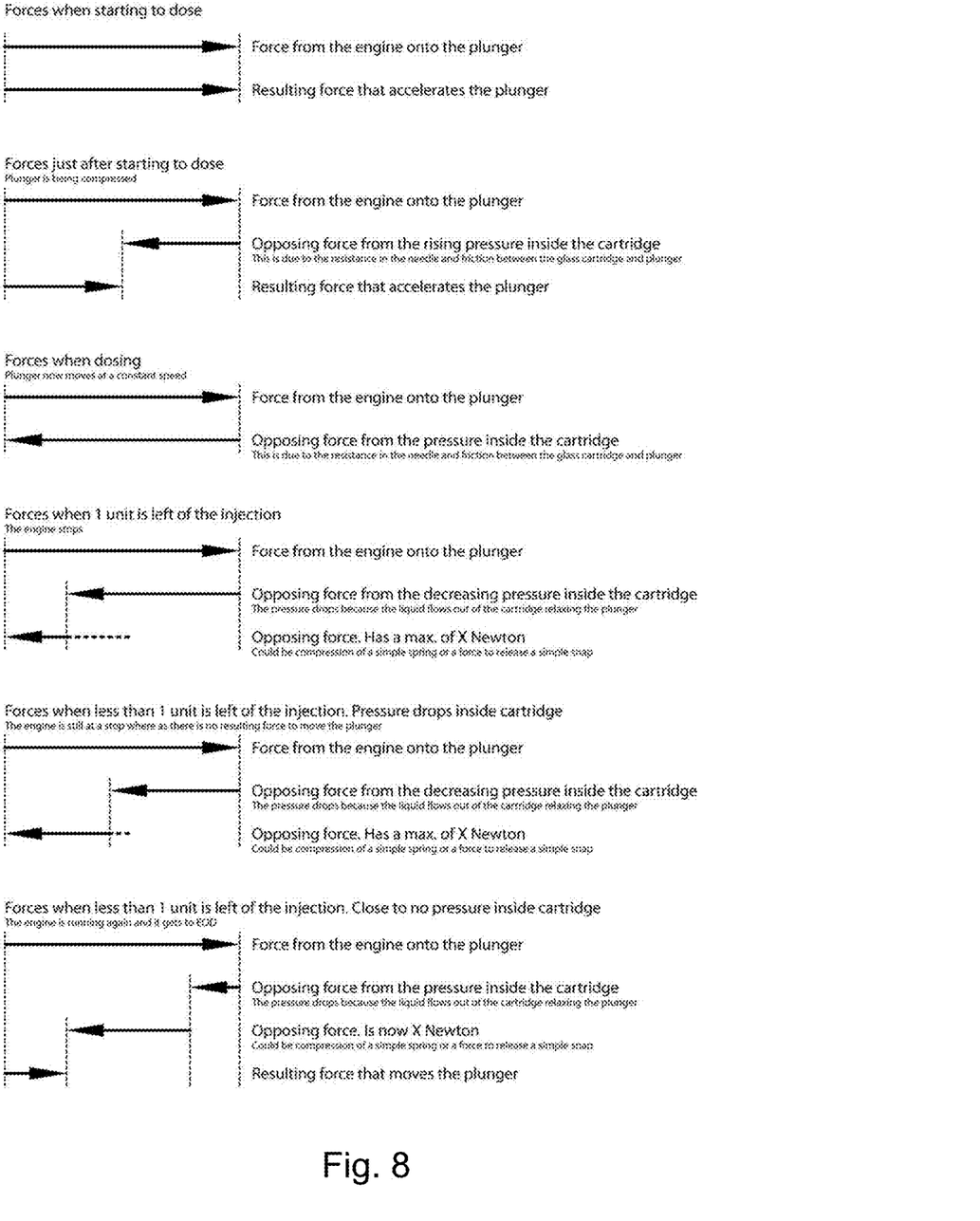
FIG. 8 an example on how the forces of the invention operate during dose expelling.

FIG. 8 is an example on how the forces of the invention operate during dose expelling.

Definitions

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

"End-of-Dose" or "EoD" mechanism is understood to be a mechanism that signals to the user once the set dose has been released. This is usually visually indicated by the return of the scale drum to its "zero" position. "Zero" position being a position in which no dose size has been selected. Alternatively, or in combination, an audible signal can be provided. For torsion spring operated injection devices such EoD signal usually indicates that the mechanics has returned to its initial state.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower neck portion into which the rubber plunger cannot be moved, not all of the drug contained inside the cartridge can be expelled. The term "initial quantum" therefore refers to the initial quantum of the injectable content.

Further the term "injection needle" defines a hollow piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 7A-J shows a schematic view of an alternative End-of-Dose mechanism relating to the injection device of FIG. 2.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not necessarily to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Figure 1:
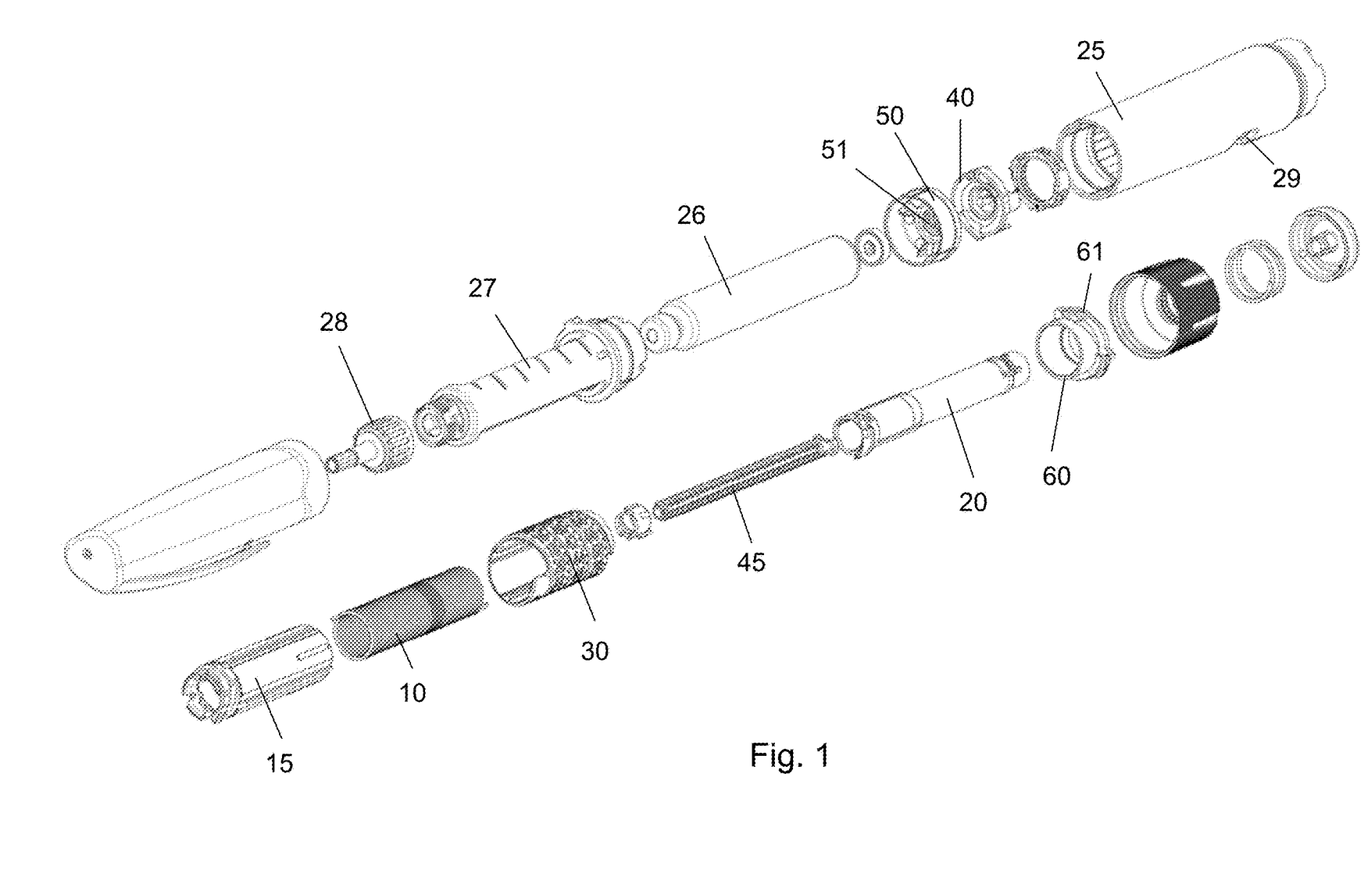
FIG. 1 shows an exploded view of the injection device according to EP application No.: 13162517.

FIG. 1 discloses a torsion spring driven injection device according to EP application No. 13162517. During injection the torque of the torsion spring 10 drives the ratchet tube 15, the reset tube 20, the scale drum 30 and the piston rod guide 40 rotational. The rotation of the piston rod guide 40 rotates the piston rod 45 in the distal direction in the internal thread 51 of the nut element 50 thereby pressing the liquid drug out from a cartridge 26 embedded in a cartridge holder 27 through the attached injection needle 28. The cartridge holder 27 is in the disclosed embodiment permanently secured to the housing 25, thus the depicted injection device being a so-called pre-filled injection device.

During dose setting, the scale drum 30 perform a helical movement in the distal direction, and during dose ejection, the scale drum 30 rotates back in the proximal direction.

During injection the scale drum 30 thus rotate back to its initial position thereby abutting the spring base 60 which is fixed to the housing 25. The spring base 60 is further provided with a click arm 61 which is strained or tighten as the scale drum 30 approaches its "zero" position and released by a countersunk surface 31 on the scale drum 30 as the scale drum 40 enters into its "zero" position. The release of the click arm 61 provides the user with an audible signal indicating that the "zero" position has been reached and the injection accomplished. In the "zero" position the number "zero" printed on the scale drum 30 is viewable in the window 29 of the housing 25.

Figure 2:
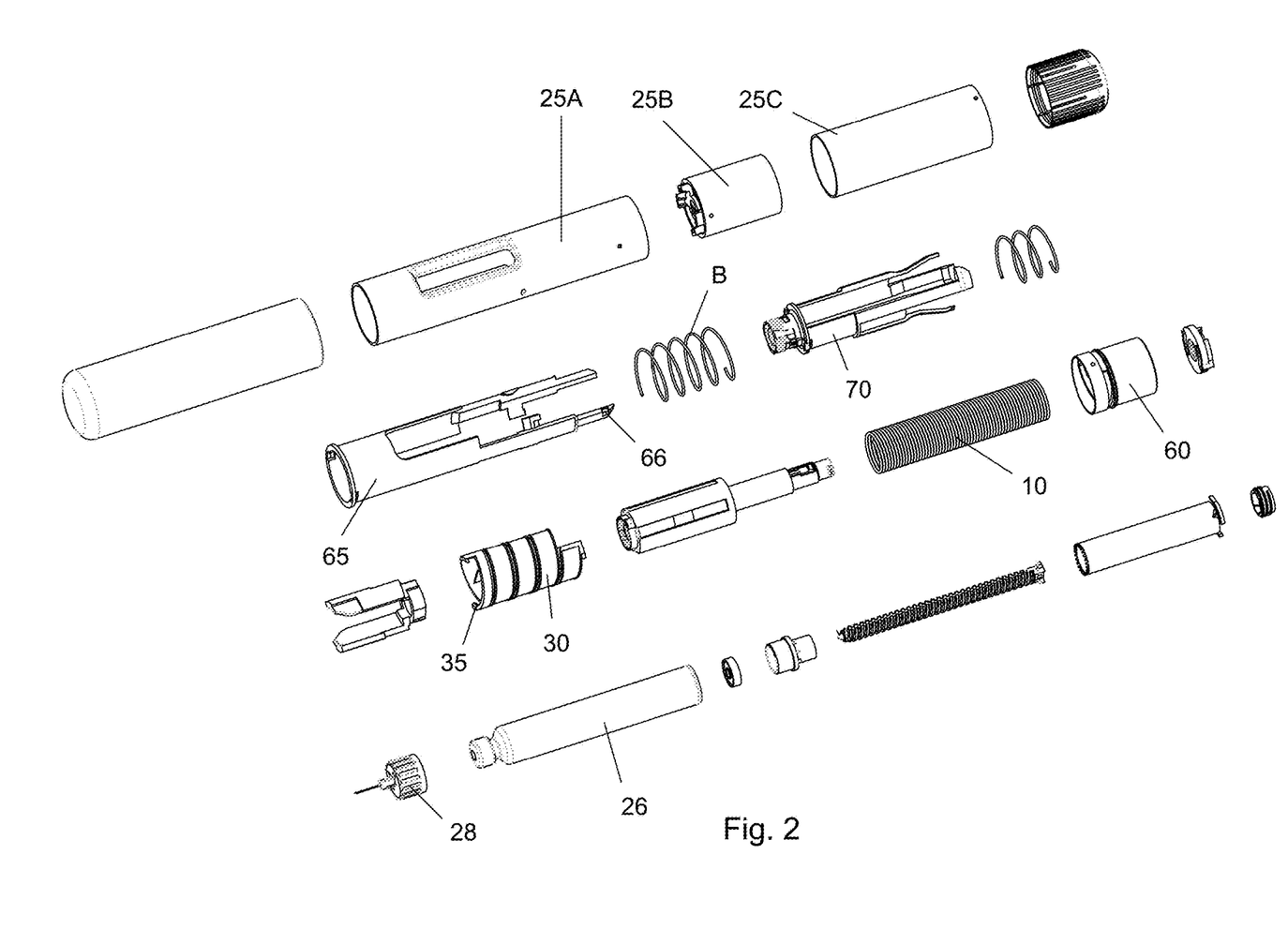
FIG. 2 shows an exploded view of the injection device according to WO 2014/001319.
Figure 3:
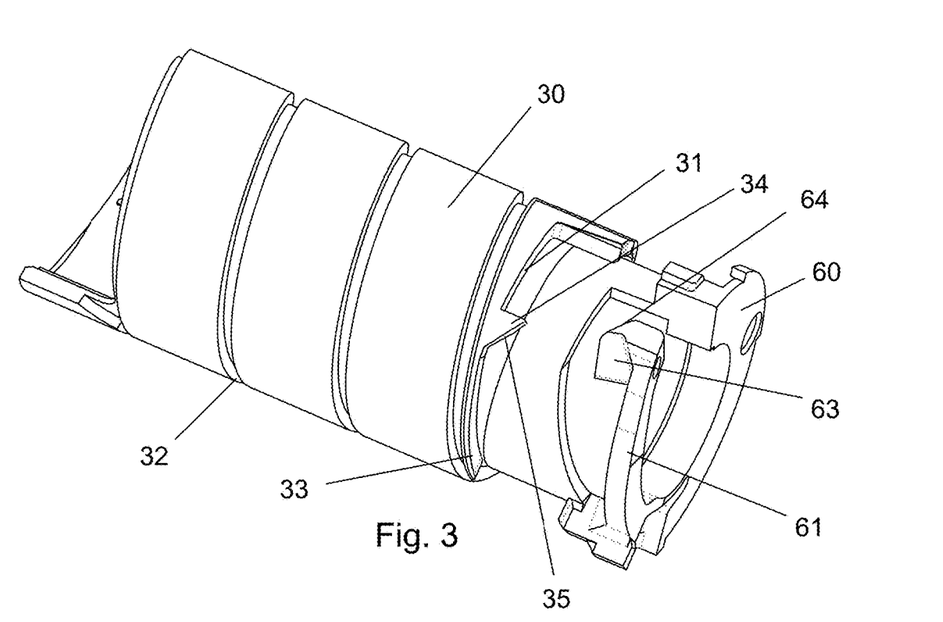
FIG. 3 shows a view of the scale drum of FIG. 1 during injection.

In the shield triggered torsion spring injection device disclosed in FIG. 2, the scale drum 30 rotate opposite such that the scale drum 30 move proximally during dose setting and distally during expelling of the set dose. This injection device is further described in WO 2014/001319.

In the following, the invention will be explained in relation to the two automatic torsion spring injection devices described in the above mentioned patent applications.

FIG. 3 to FIG. 6 relates to FIG. 1 and discloses the interaction between the scale drum 30 and the spring base 60 as the scale drum 30 returns to its initial "zero" position. In these figures, the scale drum 30 rotates counter-clockwise during dose expelling (when seen from the proximal end) around its own axis (as indicated by the arrow "I" in FIG. 4) and graduately approaches its initial position (FIG. 6) with a zero showing in the window 29. In the initial position of FIG. 6, the first surface 36 on the scale drum 30 abuts the second surface 65 on the spring mount 60. As explained later, the spring base 60 is fixed in relation to the housing 25.

The spring base 60 which secures the torsion spring 10 to the housing 25 is attached to the housing 25 via a number of protrusions 62, but could alternatively be moulded as an integral part of the housing 25.

Further, the spring base 60 carries a strainable click arm 61 which at its free end is provided with a distally pointing protrusion 63 having a sloped surface 64.

The scale drum 30 has an external thread 32 which engage an internal thread in the housing 25 such that when the scale drum 30 is rotated during dose setting the scale drum 30 moves helically in the distal direction and when injecting the scale drum 30 moves helically in the proximal direction until it abuts the spring base 60.

Figure 4:
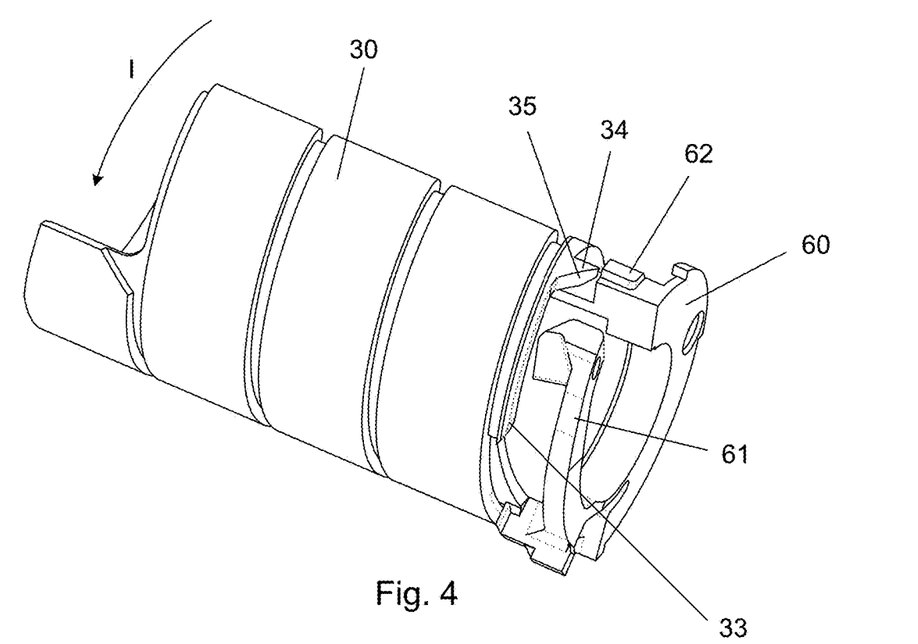
FIG. 4 shows a view of the scale drum of FIG. 1 during injection.

As the scale drum 30 approaches its initial "zero" position during injection, the ramp surface 33 provided on the scale drum 30 abuts the distal protrusion 63 on the click arm 61 thereby straining the click arm 61 in the axial direction as indicated in in FIG. 4.

Figure 5:
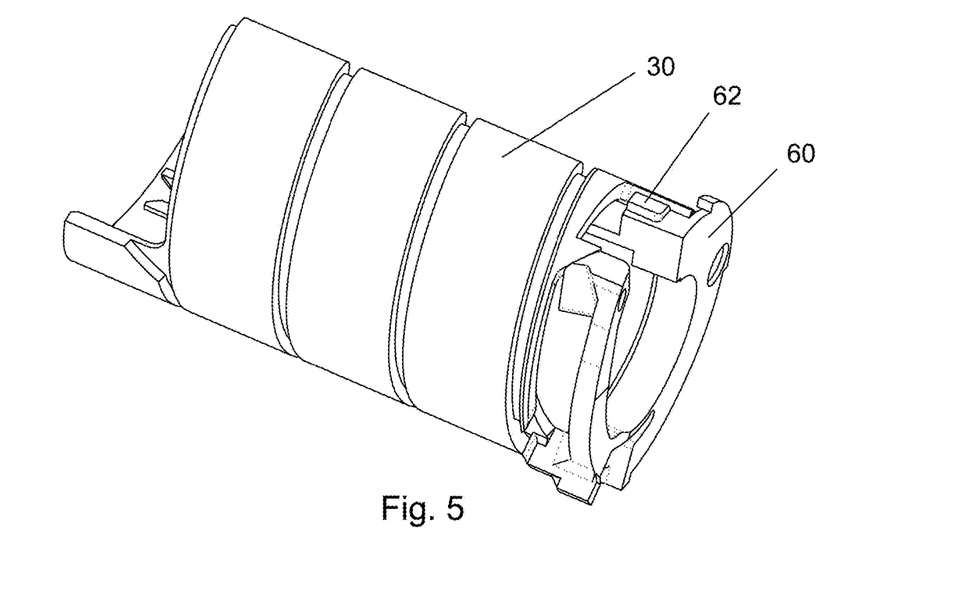
FIG. 5 shows a view of the halted scale drum of FIG. 1.

The ramp surface 33 is further provided with a stop 34 having a sloped ramp 35 which engages the sloped surface 64 on the distal protrusion 63 on the click arm 61. This abutment halts the rotational return of the scale drum 30.

The torque applied by the torsion spring 10 during injection presses the liquid drug out through the attached injection needle 28 and at the same time it rotates the scale drum 30 back to its initial position.

Figure 6:
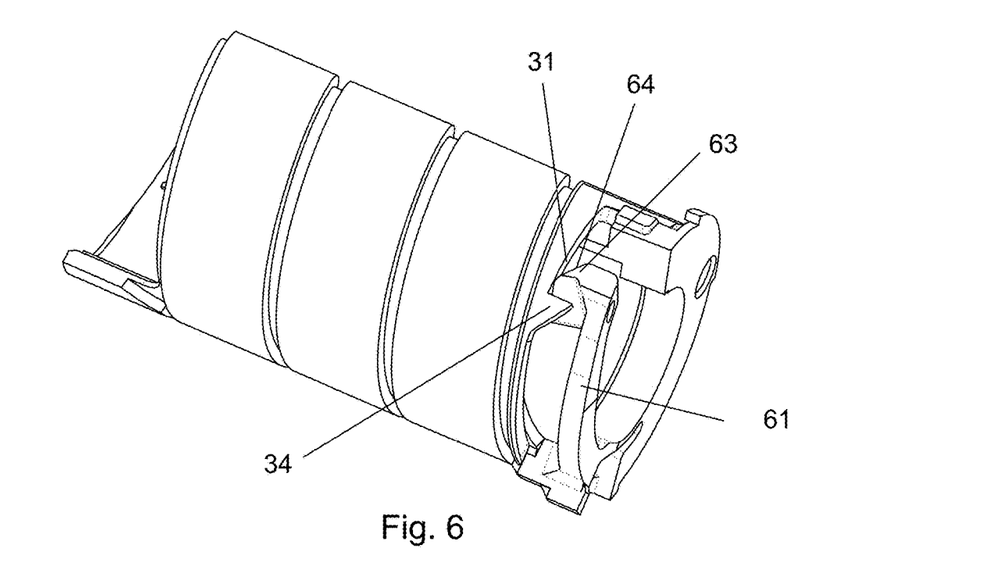
FIG. 6 shows a view of the scale drum of FIG. 1 following injection (i.e. returned to the initial position).

As the torque is released and the liquid drug starts to flow a high pressure is build up inside the cartridge 26. This high pressure generates an opposing force which the torsion spring 10 has to overcome. The result being that, when the stop 34 abuts the distal protrusion 63 on the click arm 61 it halts the further rotation of the scale drum 30 as the torque of spring 10 is utilized to overcome the opposing force from the pressure in the cartridge 26. However, once this opposing force has fallen below a certain threshold value, the remaining torque is dedicated to overcome the resistance of the stop 34 with the result that the distal protrusion 63 moves over the stop 34 and into the countersunk part 31 of the end-surface of the scale drum 30 thus generating an audible signal to the user. This signal however indicates that the pressure in the cartridge 26 (and the opposing force) has fallen below a certain threshold value indicating that the liquid drug of the set dose has been forced through the lumen of the attached injection needle 28 and dispersed into the tissue of the user.

An alternative End-of-Dose mechanism for the shield triggered injection device disclosed in FIG. 2 is further shown in FIG. 7A-C.

In this embodiment, the housing 25A, B, C comprises three different parts (A, B and C) but could easily be moulded as one or two unitary parts.

The shield 80 shielding the injection needle 28 and triggering the injection is as disclosed in WO 2014/001319 proximately provided with cut-outs 66 which engages with similar hooks 37 provided on the scale drum 30 such that the scale drum 30 locks the shield 80 in its retracted position when no dose has been set. This is the position disclosed in FIG. 7A.

When a user sets a dose (FIG. 7B) the scale drum 30 is rotated away from its initial "zero" position which releases the shield 80. The scale drum 30 moves helically in the proximal direction when a dose is dialed. The initial position ("zero") is defined by the end surface 38 on the scale drum 30 abutting the housing element 77 as disclosed in FIGS. 7A (and 7H, I, J). In this position a zero is shown in the window 29. The abutting surface 77 could be any surface which is rotational secured in relation to the housing 25. It could e.g. be a surface on the shield 80.

The compression spring B urges the shield 80 into a position in which it covers the injection needle 28 as depictured in FIG. 7C. The direction of the movement of the shield 80 is indicated by the arrow S. The needle holder 70 is moved distally by a different compression spring C.

In FIG. 7D, the desired dose has been reached. The needle holder 70 which during dose setting remains in the same position is proximately provided with an extension 71. Further, a housing part 75 is provided with a guide arm 76.

During injection as disclosed in FIG. 7E, the shield 80 is pushed in the proximal direction as the shield 80 abuts the skin of the user. The shield 80 is proximally provided with a hook 67 which in this position couples to the extension 71 of the needle holder 70 as the extension 71 abuts the guide arm 76. In order to secure the extension 71 to the hook 67, the extension has a protrusion 72. Due to this protrusion 72, the extension 71 cannot move axially again before the extension 71 is moved rotational out of its engagement with the hook 67.

As the shield 80 is pushed further in the proximal direction during injection (FIG. 7F) it brings the needle holder 70 with it such that the injection needle 28 penetrates into the cartridge 26 and the automatic injection is started. During the injection the scale drum 30 automatically under influence of the torsion spring 10 rotates back to its initial "zero" position".

Just before the scale drum 30 reaches its "zero" position, the rotation of the scale drum 30 is halted by a stop 39 on the scale drum 30 encountering the proximal end of the extension 71 of the needle holder 70 as depictured in FIG. 7G. In this position the torque applied by the torsion spring 10 is dedicated to overcome the opposing force arising from the high pressure within the cartridge 26. Only when this pressure has fallen below a certain value and the opposing force has fallen, the torque dedicated to rotate the scale drum 30 becomes sufficient to release the extension 71 from the hook 67 as depictured in FIG. 7H.

The release of the extension 71 from the hook 67 and the almost simultaneously abutment of the extension 71 with the housing part 75 provides a delayed audible signal to the user indicating that the injection device can be removed from the skin of the user.

Once the injection device is removed from the skin as depictured in FIG. 7I the shield 80 slides slightly in the distal direction until the hook 37 of the scale drum 30 engages the cut-out 66 on the shield 80.

Also when removing the injection device from the skin, the needle holder 70 slides distally uncoupling the injection needle 28 from the cartridge 26 as disclosed in FIG. 7J. During the distal movement of the needle holder 70 the extension 71 is guided into its starting position by the guide arm 76. The injection device is thereafter ready for the user to set a new dose and make a new injection. FIG. 7J and FIG. 7A thus being identical.

Some preferred embodiments have been shown in the foregoing, but it should be stressed that the invention is not limited to these, but may be embodied in other ways within the subject matter defined in the following claims.

The invention claimed is:

1. An injection device for apportioning set doses of a liquid drug having an end-of-dose feedback mechanism, comprising:
    a housing,
    a dose setting mechanism rotatable operable for setting a dose to be expelled,
    a rotatable scale drum coupled to the dose setting mechanism and which scale drum is arranged to rotate away from its initial position during dose setting and rotate back to its initial position during dose expelling, the initial position being defined by a first surface on the scale drum abutting a second surface fixed in relation to the housing,
    a torsion spring which is torsional strained during dose setting and which torque is utilized to expel the set dose and to rotate the scale drum back to its initial position during dose expelling,
    an end-of-dose mechanism for generating an audible feedback signal to the user upon receipt of the rotatable scale drum in its initial position following an injection, wherein
    the injection device further is provided with a stopping structure adapted to halt the torsion spring based rotation of the scale drum prior to the scale drum reaching its initial position by the first surface on the scale drum abutting the second surface and the stopping structure further are adapted to allow the scale drum to move past the stopping structure and continue rotation when the torque applied to the scale drum passes a threshold value.

2. An injection device according to claim 1, wherein the stopping structure comprises a first element provided on the scale drum and a second element irrotatable coupled to the housing and wherein an engagement between the first element and the second element is released when the torque applied to the scale drum surpasses a threshold value and the scale drum is allowed to rotate back to its initial position.

3. An injection device according to claim 1, wherein the stopping structure halting the rotation of the scale drum comprises an extension proximally extending an axial movable part of the injection device.

4. An injection device according to claim 3, wherein the movable part is a needle holder which moves axially in relation to a cartridge during injection.

5. An injection device according to claim 3, wherein the injection device is provided with a locking structure for locking the extension during its axial movement.

6. An injection device according to claim 5, wherein the locking structure comprises a hook provided on a telescopically movable shield.

7. An injection device according to claim 6, wherein the shield and the needle holder move axially during injection.

8. An injection device according to claim 1, wherein the stopping means halting the rotation of the scale drum comprises a stop on the scale drum.

9. An injection device according to claim 8, wherein the stop is arrested by a flexible arm secured to the housing.

10. An injection device according to claim 9, wherein the flexible arm at its free end is provided with a distally pointing protrusion.

11. An injection device according to claim 8, wherein the scale drum is provided with a countersunk area.

\* \* \* \* \*